United States Patent [19]

Gyory et al.

[11] Patent Number: 5,883,135
[45] Date of Patent: Mar. 16, 1999

[54] COMPOSITION, DEVICE, AND METHOD FOR ENHANCED ELECTROTRANSPORT AGENT DELIVERY

[75] Inventors: J. Richard Gyory, San Jose; Jane Yieh, Millbrae, both of Calif.; James A. Huntington, Chicago, Ill.; Michel Cormier, Mountain View, Calif.

[73] Assignee: ALZA Corporation, Palo Alto, Calif.

[21] Appl. No.: 846,225

[22] Filed: Apr. 28, 1997

Related U.S. Application Data

[62] Division of Ser. No. 339,092, Nov. 14, 1994.
[51] Int. Cl.$^6$ ............ A61K 31/045; A61K 31/07; A61K 38/00
[52] U.S. Cl. .............. 514/724; 514/2; 514/725
[58] Field of Search .................. 514/724, 725, 514/2

[56] References Cited

U.S. PATENT DOCUMENTS

| | | |
|---|---|---|
| 4,250,878 | 2/1981 | Jacobsen et al. . |
| 4,593,048 | 6/1986 | Sato et al. . |
| 4,615,699 | 10/1986 | Gale et al. . |
| 4,645,502 | 2/1987 | Gale et al. . |
| 4,692,328 | 9/1987 | Kitchell et al. . |
| 4,722,726 | 2/1988 | Sanderson et al. . |
| 4,752,612 | 6/1988 | Saito et al. . |
| 4,927,408 | 5/1990 | Haak et al. . |
| 5,002,956 | 3/1991 | Thiel . |
| 5,023,085 | 6/1991 | Francoeur et al. . |
| 5,080,646 | 1/1992 | Theeuwes et al. . |
| 5,125,894 | 6/1992 | Phipps et al. . |
| 5,147,296 | 9/1992 | Theeuwes et al. . |
| 5,162,042 | 11/1992 | Gyory et al. . |
| 5,169,382 | 12/1992 | Theeuwes et al. . |
| 5,169,383 | 12/1992 | Gyory et al. . |
| 5,221,254 | 6/1993 | Phipps . |
| 5,232,438 | 8/1993 | Theeuwes et al. . |
| 5,234,992 | 8/1993 | Gyory et al. . |
| 5,240,495 | 8/1993 | Gyory et al. . |
| 5,298,017 | 3/1994 | Theeuwes et al. . |
| 5,312,439 | 5/1994 | Loeb . |
| 5,322,502 | 6/1994 | Theeuwes et al. . |
| 5,344,394 | 9/1994 | Gyory et al. . |
| 5,356,632 | 10/1994 | Gross et al. . |
| 5,380,271 | 1/1995 | Gyory . |
| 5,403,275 | 4/1995 | Phipps . |

FOREIGN PATENT DOCUMENTS

| | | |
|---|---|---|
| 0 043738 A3 | 1/1982 | European Pat. Off. . |
| 0 267617 A1 | 5/1988 | European Pat. Off. . |
| 0 290262 A2 | 11/1988 | European Pat. Off. . |
| 0 552879 A1 | 7/1993 | European Pat. Off. . |
| WO91/16930 | 11/1991 | WIPO . |

OTHER PUBLICATIONS

Chemical Abstracts (118:154571) Farhadick et al., Transdermal albuterol patches 1992.

Srinivasan, V., et al., Journal of Pharmaceutical Sciences, vol. 79, No. 7, Jul. 1990, pp. 588–591, Iontophoresis of Polypeptides: "Effect of Ethanol Pretreatment of Human Skin".

Rolf, David, Pharmaceutical Technology, Sep. 1988, pp. 130–138, "Chemical and Physical Methods of Enhancing Transdermal Drug Delivery".

Kontturi et al., Pharmaceutical Research, vol. 10, No. 3, 1993, pp. 381–385, "Electrochemical Characterization of Human Skin by Impedance spectroscopy: The Effect of Penetration Enhancers".

Cullander, Christopher, Advanced Drug Delivery Reviews, 9 (1992), pp. 119–135, "What are the pathways of iontophoretic current flow through mammalian skin?"

Hirvonen, J., et al., Proceed, Intern. Symp. Control. Rel. Bioact. Mater., 19 (1992), Controlled Release Society, Inc., pp. 452–453, "Transdermal Permeation of Model Anions and Cations; Effect of Skin Charge, Iontophoresis and Penetration Enhancers".

Del Terzo, Sam, et al., Pharmaceutical Research, col. 6, No. 1, 1989, pp. 85–90, "Iontophoretic Transport of a Homologous Series of Ionized and Nonionized Model Compounds: Influence of Hydrophobicity and Mechanistic Interpretation".

Ferber, et al., Abstract: Pharmaceutical Research, Sep. 1990 (Suppl.), vol. 7, No. 9, PDD 7256, "Alkanol Enhancement of Transdermal Penetration of Water Soluble Compounds".

Indian J. Pharm. Sci., vol. 56, No. 6, Nov. 1994, pp. 205–209, XP 000563597, Chandrasekar, G.; et al., "Optimization of Parameters for Transdermal Permeation of Insulin".

Barry, B.W., Journal of Controlled Release, 6 (1987) pp. 85–97, "Mode of Action of Penetration Enhancers in Human Skin".

Behl, et al., Journal of Pharmaceutical Sciences, vol. 78, No. 5, (1989) pp. 355–360, "Iontophoretic Drug delivery: Effects of Physicochemical Factors on the Skin Uptake of Nonpeptide Drugs."

*Primary Examiner*—Kevin E. Weddington
*Attorney, Agent, or Firm*—D. Byron Miller; Michael J. Rafa; Steven F. Stone

[57] ABSTRACT

An electrotransport composition comprises at least one $C_2$–$C_4$ lower alcohol, unsaturated derivatives thereof, or mixtures thereof, and at least one $C_8$–$C_{14}$ higher alcohol, unsaturated derivatives thereof, or mixtures thereof. An electrotransport device and a method of increasing transdermal electrotransport flux utilize the composition of the invention for delivering pharmaceutically-acceptable agents across a body surface such as skin.

12 Claims, 1 Drawing Sheet

COMPOSITION, DEVICE, AND METHOD FOR ENHANCED ELECTROTRANSPORT AGENT DELIVERY

This application is a divisional of application Ser. No. 08/339,092, filed Nov. 14, 1994.

BACKGROUND OF THE INVENTION

1. Technical Field

This invention relates generally to-permeation enhancers for electrotransport agent delivery. More particularly, this invention relates to compositions comprising different alcohols as permeation enhancers. These compositions may be incorporated into electrotransport devices for the delivery of agents, such as drugs and prodrugs, through a body surface.

2. Background Art

Drugs are most conventionally administered either orally or by injection. Unfortunately, many medicaments are completely ineffective or of radically reduced efficacy when orally administered since they either are not absorbed or are adversely affected before entering the blood stream and thus do not possess the desired activity. On the other hand, the direct injection of the medicament into the blood stream, while assuring no modification of the medicament in administration, is a difficult, inconvenient and uncomfortable procedure, sometimes resulting in poor patient compliance. Transdermal drug delivery offers improvements in these areas. The term "transdermal" is used herein in its broadest sense as the delivery of an agent through a body surface, such as the skin, mucosa, or nails. There are two major types of transdermal agent delivery, one driven by a concentration-gradient force (passive transdermal delivery), and the other driven, in addition, by a force created by applying an electrical potential (electrotransport delivery).

The tern "passive" transdermal delivery, is used herein to describe the passage of an agent through a body surface, eg, skin, in the absence of an applied electrical current. Typically, passive delivery devices have a drug reservoir which contains a high concentration of a drug. The device is placed in contact with a body surface for an extended period of time, and is allowed to diffuse from the reservoir and into the body of the patient, which has a much lower concentration of drug. The primary driving force for passive drug delivery is the concentration gradient of the drug across the skin. In this type of delivery, the drug reaches the bloodstream by diffusion through the dermal layers of the body. The preferred agents for passive delivery are hydrophobic non-ionic agents, given that the drug must diffuse through the lipid layers of the skin.

The term "electrotransport" is used herein to describe the passage of a substance, eg, a drug or prodrug, through a body surface or membrane, such as the skin, mucous membranes, or nails, induced at least partially by the application of an electric field across the body surface (eg, skin). A widely used electrotransport process, iontophoresis, involves the electrically induced transport of therapeutic agents in the form of charged ions. Ionizable therapeutic agents, eg, in the form of a salt which when dissolved forms charged agent ions, are preferred for iontophoretic delivery because the charged agent ions move by electromigration within the applied electric field. Electroosmosis, another type of electrotransport process, involves the movement of a liquid, which liquid contains a charged and/or uncharged therapeutic agent dissolved therein, through a biological membrane under the influence of an electric field. Another type of electrotransport, electroporation, involves the formation of transiently-existing pores in a living biological membrane under the influence of an electric field and delivery of a therapeutic agent therethrough. However, in any given electrotransport process, more than one of these processes may be occurring simultaneously to some extent. Accordingly, the term "electrotransport" is used herein in its broadest possible interpretation to include the electrically induced or enhanced transport of at least one agent, which may be charged, ie, in the form of ions, or uncharged, or of mixtures thereof, regardless of the specific mechanisms by which the agent is actually transported.

A common goal in both passive and electrotransport delivery is to enhance the rate of delivery of the agent. A further goal in electrotransport delivery is to reduce the electrical resistance of the skin or other body surfaces, so that the power requirements for a given level of applied electric current or drug flux will be lowered. The term "permeation enhancer" is used herein to describe additives which cause an increase in drug delivery rates both in passive and electrotransport delivery, regardless of whether the enhancement occurs by reduction of electrical or diffusional resistance.

Although there are similarities between electrotransport and passive transdermal delivery, there are also substantial differences. One difference relates to the different pathways utilized for delivery through the skin by the passive and electrotransport induced processes. Transdermal electrotransport delivery of an agent occurs within the hydrophilic pathways through the skin, ie, the sweat ducts, around hair follicles, and/or through pores, because these are the paths of least electrical resistance. On the other hand, passive transdermal delivery occurs primarily by direct diffusion through the lipid layers of the skin. Accordingly, an ideal passive permeation enhancer will disrupt the lipid layers of the skin, while an ideal electrotransport enhancer will preferably decrease the electrical resistance of the existing hydrophilic pathways in the skin. (See, Rolf, D., "Chemical and Physical Methods of Enhancing Transdermal Drug Delivery," Pharmaceutical Technology, pp 130–140 (September 1988); Cullander, C., "What are the Pathways of Iontophoretic Current Flow through Mammalian Skin", Advanced Drug Delivery Reviews, 9:119–135 (1992)).

Thus, it is not surprising that many passive permeation enhancers do not enhance electrotransport delivery rates. For instance, Hirvonen et al indicate that N, N-dimethylamino acetate (DDM) and azone increase the rate of passive permeation of the agent sotalol relative to that obtained with sotalol alone (control). (Hirvonen et al, "Transdermal Permeation of Model Anions and Cations: Effect of Skin Charge, Iontophoresis and Permeation Enhancers", Proceed. Intem. Symp. Control. Rel. Bioact. Mater., 19:452 (1992)). And the passage of an electric current was also shown to increase the rate of delivery of sotalol compared to that of its passive rate (control). However, the addition to solatol of either DDAA or azone reduced the rate of electrotransport of solatol compared to its rate of electrotransport without DDAA or azone (control). Clearly, DDAA and azone, both known passive permeation enhancers, were not only inoperative in electrotransport, but they actually reduced the rate of electrotransport delivery of the agent. Kontturi et al indicated that the aforementioned passive enhancers, in fact, increase skin resistivity, and advanced that passive enhancers such as those are inappropriate for use in electrotransport drug delivery. (Kontturi et al, "Electrochemical Characterization of Human Skin by Impedance Spectroscopy: The Effect of Penetration Enhancers", Pharmaceutical Research 10(3):381–385 (1993)).

Other permeation enhancers have been disclosed to be useful in passive transdermal delivery. For example, WIPO Laid Open Patent Application WO 91/16930 to Ferber et al discloses that an aqueous solution of up to 40 v/v% lower alcohol and higher alcohol in a saturating amount is suitable for enhancing passive transdermal delivery. Suitable passive transdermal delivery enhancers disclosed therein are lower $C_2$–$C_4$ alcohols such as ethanol, 1-propanol, 2-propanol, 1-butanol, and 2-butanol, and higher alcohols such as $C_6$–$C_{14}$ alcohols including 1-hexanol, 1-octanol, 1-nonanol, 1-decanol, 1-undecanol, 1-dodecanol, 1-tidecanol, 1-tetradecanol, 4-methyl-1-pentanol, 5-methyl-1-heptanol, 3,3-dimethyl-1-octanol, 3-cyclopentyl-1-propanol, cis-3-hexen-1-ol, trans-3-hexen-1-ol, 9-decen-1-ol and 2-octanol.

The number of permeation enhancers disclosed as useful in electrotransport delivery is considerably more limited. Ethanol, for instance, has been used as a permeation enhancer for the electrotransport delivery of polypeptides is discussed by Srinivasan et al (Srinivasan et al, "Iontophoresis of Polypeptides: Effect of Ethanol Pretreatment of Human Skin," J. Pharm. Sci. 79(7):588 (July 1990)). Surfactant (eg, sodium lauryl sulfate) permeation enhancers for electrotransport drug delivery are disclosed in Sanderson et al, U.S. Pat. No. 4,722,726 and fatty acid (eg, oleic acid) permeation enhancers for electrotransport drug delivery are disclosed in Francoeur et al, U.S. Pat. No. 5,023,085.

Thus, in general, there is still a need for compositions which reduce the electrical resistance of the skin and, thus, increase agent electrotransport therethrough, producing an enhancement of the delivery rate of the agent while reducing the power requirements of the electrotransport device and/or the area of contact between the device and the body surface.

DISCLOSURE OF THE INVENTION

This invention arose from a desire to improve on prior art technology in the field of transdermal electrotransport delivery. This invention provides a composition that enhances the electrotransport flux of a drug or prodrug through a body surface such as skin. The permeation enhancing composition comprises in combination (1) at least one lower alcohol and (2) at least one higher alcohol, both of which may be linear branched, aromatic, and/or cyclic. The lower alcohol is preferably a $C_2$–$C_4$ alkanol or unsaturated derivatives thereof, and more preferably ethanol. The higher alcohol is preferably a $C_8$–$C_{14}$ alkanol or unsaturated derivatives thereof, more preferably a $C_{10}$–$C_{12}$ alkanol or unsaturated derivatives thereof. Of these higher alcohols, dodecanol and 1-dodecanol are most preferred.

The composition of the invention reduces the electrical resistance of body surfaces, such as the skin, mucosa, and nails, during electrotransport agent delivery, and permits a reduction in the size of the delivery device and/or the power (ie, voltage) required to maintain a particular level of electrotransport current and rate of electrotransport agent delivery.

The present composition is suitable for use in reducing the electrical resistance of the body surface (eg, skin) site adjacent the donor electrode of an electrotransport delivery device, the skin site adjacent the counter electrode of the device, or both body surface sites. The permeation enhancer composition may be applied to the body surface prior to or during agent delivery, but the composition is preferably placed in the donor and/or counter reservoir of an electrotransport delivery device and is delivered to the body surface simultaneously with the agent.

Also provided herein is an electrotransport delivery device comprising donor and counter electrodes, at least one of the electrodes having a reservoir comprising the lower/higher alcohol composition, an electrical power source which is electrically connected to the donor and counter electrodes, and optionally electronic control circuitry.

The composition of the present invention may be used with different electrotransport devices for the delivery of a variety of pharmaceutically acceptable agents, including those specifically disclosed herein. One particular application for which the composition is most suitable is the electrotransport delivery of amine and amino acid containing agents.

This invention will now be described in further detail with reference to the accompanying drawing.

MODES FOR CARRYING OUT THE INVENTION

Figure 1:
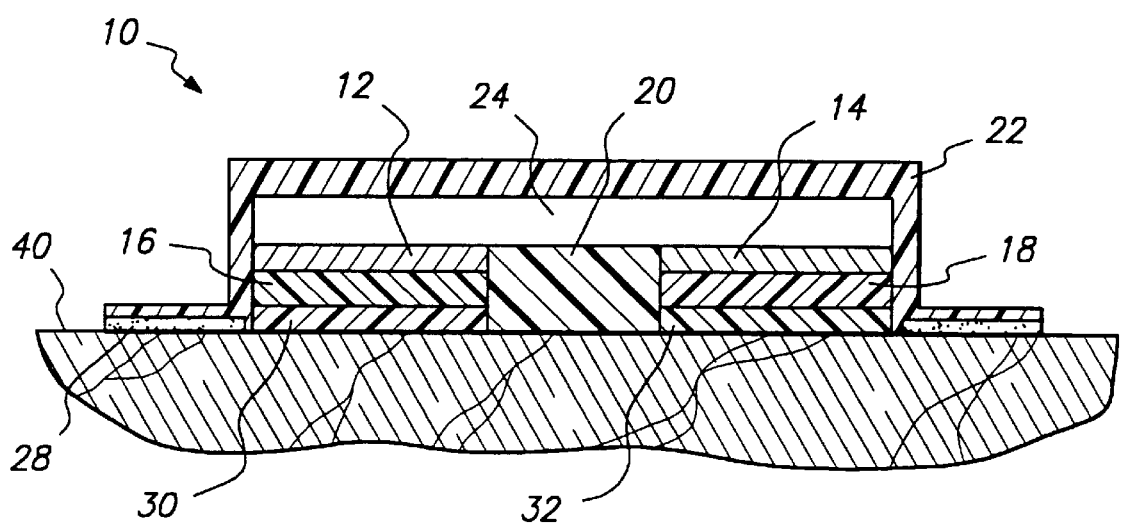
FIG. 1 is a sectional view of one embodiment of an electrotransport device suitable for use with the permeation enhancing composition of the present invention.

This invention arose form a desire to improve on prior art technology for the transdermal delivery of pharmaceutically-acceptable agents, such as drugs or prodrugs, suitable for the prevention or treatment of disease in humans. The present technology has particular application in the field of electrotransport delivery of pharmaceutically-acceptable agents (eg, drugs) and particularly agents containing amine groups and/or peptide groups.

This present invention, thus, provides a transdermal electrotransport permeation enhancing composition, comprising at least one lower alcohol, preferably a $C_2$–$C_4$ alkanol or unsaturated derivatives thereof, or mixtures thereof, and at least one higher alcohol, preferably a $C_8$–$C_{14}$ alkanol or unsaturated derivative thereof, or mixtures thereof. An alcohol, as used herein, is defined as an alkyl compound having at least one hydroxyl (—OH) group, which may be saturated or unsaturated, linear, branched, cyclic and/or aromatic. This definition also includes polyhydric alcohols having more than one hydroxyl group, such as glycols or diols. A "higher alcohol", as used herein, refers to a straight or branched chain or cyclic $C_8$–$C_{14}$ alcohol. The higher alcohol may be a primary, secondary or tertiary alcohol. Examples of higher alcohols include, without limitation, 1-dodecanol, 3-dodecanol, 1-decanol, 1-undecanol, 3-butyl-1-octanol, 4-pentyl-1-hexanol, and 5-propyl-2-decanol. The higher alcohol is preferably a straight chain alcohol having 10 to 12, and more preferably 12, carbon atoms. Preferred as a higher alcohol is dodecanol, and still more preferred is 1-dodecanol. A "lower alcohol", as used herein, encompasses an alcohol preferably having 2 to 4 carbon atoms. The lower alcohol may be a primary, secondary or tertiary alcohol including, without limitation, ethanol, 1-propanol, 2-propanol, 1-butanol, 2-butanol, t-butyl alcohol, and unsaturated derivatives thereof. More preferably, the lower alcohol is ethanol or propanol, and still more preferably it is ethanol. The alcohols of the composition of this invention may have other substituents which do not interfere with the electrotransport delivery enhancing characteristics of the composition. The combination of the lower and higher alcohols in an electrotransport composition produces an unexpected enhancement of the transdermal electrotransport drug flux, which is accompanied by an unexpected reduction in skin resistance during electrotransport drug delivery, when compared with the drug flux and skin resistance when electrotransporting drug in the presence of either the lower alcohol or the higher alcohol alone.

An increase in the delivery rate of the agent and a decrease in the electrical resistance of the body surface are achieved by contacting the agent (eg, drug) to be delivered and the composition with the body surface while applying an electrical current through the composition, the agent, and the body surface. More preferably, the composition of the invention is added directly to the donor reservoir, counter reservoir, or both reservoirs of an electrotransport delivery device. However, the body surface may also be treated with the lower/higher alcohol composition prior to the electrotransport delivery of the drug. In addition, it is possible to apply the lower/higher alcohol composition to the body surface after electrotransport delivery of the agent has been initiated.

The concentration of the higher alcohol in the fully hydrated donor reservoir, ie, under reservoir conditions immediately prior to use, is preferably about 0.01 to 100 millimolar (mM). More preferably, the higher alcohol concentration is about 1 to about 50 mM, and still more preferably greater than 10 mM. The concentration of the lower alcohol in the donor reservoir is preferably about 0.5 to 30% (v/v), more preferably less than about 25% (v/v), and still more preferably, 10 to 25% (v/v). In one particularly preferred form of the device, the composition present in the donor reservoir preferably contains sufficient water to achieve greater than to 50% ionization of the agent to be delivered. The concentration of the pharmaceutically-acceptable agent to be delivered may vary substantially, depending on the type of drug, its potency, and the like. The concentration of the agent in the fully hydrated donor reservoir is generally about 1 microgram/mL ($\mu$g/mL) to 100,000 $\mu$g/mL, and more preferably about 1000 $\mu$g/mL to about 50,000 $\mu$g/mL. Furthermore, the donor reservoir may contain other chemical species such as buffering agents, antioxidants, antimicrobial agents and agents that further increase the conductivity of the body surface or its permeability, and the like. Other suitable additives may be chosen to increase drug solubility and/or increase charged ion concentration. The donor reservoir may also contain additives which inhibit microbial growth or perform other functions unrelated to the delivery of the agent.

This invention is useful in the delivery of drugs or prodrugs within a broad class that are deliverable through body surfaces and membranes, including the skin, mucosa and nails. As used herein, the expressions "agent", "drug" and "prodrug" are used interchangeably, and are intended in their broadest interpretation as any pharmaceutically-acceptable substance which may be delivered to a living organism to produce a desired, usually beneficial, effect. In general, this includes therapeutic agents in all of the major therapeutic fields including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetrics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetrics; prostaglandins; proteins; peptides; psychostimulants; sedatives and tranquilizers.

More specifically, this invention is useful for the controlled delivery of baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil, among other drugs.

The invention is particularly useful in the controlled delivery of peptides, polypeptides, proteins, or other macromolecules difficult to deliver transdermally or transmucosally because of their size. These macromolecular substances typically have a molecular weight of at least about 300 Daltons, and more typically, in the range of about 300 to 40,000 Daltons. Examples of peptides and proteins which may be delivered in accordance with the present invention include, without limitation, LHRH, LHRH. analogs such as buserelin, gonadorelin, naphrelin and leuprolide, GHRH, GHRF, insulin, insulinotropin, heparin, calcitonin, octreotide, endorphin, TRH, NT-36 (chemical name: N-[[(s)-4-oxo-2-azetidinyl]carbonyl]-L-histidyl-L-prolinamide], liprecin, pituitary hormones (eg, HGH, HMG, HCG, desmopressin acetate), follicle luteoids, $\alpha$-ANF, growth factor releasing factor (GFRF), $\beta$-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirudin and hirudin analogs such as hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

One example of an electrotransport device suitable for use with the present invention is illustrated in FIG. 1. Device 10 has two current distributing members or electrodes, comprised of electrically conductive materials, referred to herein as donor electrode 12 and counter electrode 14. The electrodes may be composed of any materials which are sufficiently electrically conductive, including without limitation, silver, silver chloride, zinc, carbon, and stainless steel. The electrodes may be present in a variety of forms including a metal foil or screen, a polymer film having an electrically conductive coating or a polymer matrix containing an electrically conductive filler, eg, powdered carbon or metal, formed by conventional processes such as extruding, calendering, film evaporation, or spray coating. In FIG. 1, the donor and counter electrodes 12 and 14 are positioned adjacent to, and in electrical contact with, donor reservoir 16 and counter reservoir 18, respectively. The donor reservoir 16 contains a solution of the beneficial agent (eg, a drug) to be delivered, while the counter reservoir 18 contains a solution of a biocompatible electrolytic salt such as sodium chloride or optionally another beneficial agent to be delivered. The reservoirs 16 and 18 are formed of any material adapted to absorb and hold a sufficient quantity of liquid therein in order to permit the passage of the agent therethrough by electrotransport. Since water is the preferred liquid solvent for forming the solutions contained in reservoirs 16 and 18, the reservoirs preferably contain one or more hydrophilic polymers such as polyvinylpyrrolidone, polyvinyl alcohol, or polyethylene glycols, optionally mixed with a hydrophobic polymer such as polyisobutylene, polyethylene, and/or polypropylene. An electrical insulator 20 is positioned between (i) the donor electrode 12 and the donor reservoir 16, and (ii) the counter electrode 14 and the counter reservoir 18. The insulator 20, may be an air gap or a material which conducts neither electrons nor ions to a substantial extent, and prevents the device 10 from short-circuiting through a path which does not include the body surface 40, to which the device 10 is applied. The device 10 optionally includes a backing layer 22 composed of a liquid-impermeable non-conducting material.

The device 10 has an electronic circuit, illustrated schematically in FIG. 1 as layer 24, having an electric power source, eg, one or more batteries, therein. Typically, the electronic circuit layer 24 is relatively thin and is preferably comprised of electronically conductive pathways, which are printed, painted or otherwise deposited on a thin, flexible substrate such as, for example, a film or polymeric web. The electronic circuit layer 24 is, for example, a printed flexible circuit. In addition to the power source, the electronic circuit layer 24 may also include one or more electronic components which control the level, waveform shape, polarity, timing, etc, of the electric current applied by the device 10. For example, the circuit layer 24 may contain one or more elements of control circuitry such as a current controller, eg, a resistor or a transistor-based current control circuit, an on/off switch, and/or a microprocessor adapted to control the current output of the power source over time. The outputs of the circuit layer 24 are electrically connected to the electrodes 12 and 14, so that at any one time each electrode is in electrical contact with an opposite pole of the power source within the circuit layer 24.

In this embodiment, the device 10 adheres to the body surface by means of a peripheral adhesive layer 28. The device may optionally contain an in-line adhesive layer, ie an ion-conducting adhesive layer positioned between reservoirs 16, 18 and the body surface, eg, the skin surface. An in-line adhesive must be composed of an ion-transmitting material, ie beneficial agent ions must be capable of passing through the adhesive layer to reach the body surface. Optional flux control membranes 30 and 32, such as those disclosed in Theeuwes et al, U.S. Pat. Nos. 5,080,646; 5,147,296; and 5,169,382, are positioned between the donor reservoir 16 and the body surface 40 and between the counter reservoir 18 and the body surface 40, respectively, in order to limit or control the amount of passive, ie non-electrically assisted, flux of agent to the body surface 40.

The invention will be further described by reference to the following examples, wherein human cadaver skin electrical resistivity and drug flux were measured for various permeation enhancer compositions.

EXAMPLES

Preparation of Human Cadaver Skin

Skin strips having a thickness of 1 mm were removed from a human cadaver with an electric dermatome. These skin strips were placed in polyethylene bags, sealed and placed in a refrigerator at 4° C. for temporary storage. Prior to use in an electrotransport cell, the skin strips were placed in 1 liter beakers containing water at 60° C. for about 90 seconds, and gently stirred. The skin strips were then removed, and placed onto the absorbent side of a piece of BENCHKOTE fabric with their dermis side down. The epidermis was removed from each strip with a round-tip spatula, and flat tipped tweezers to retain the dermis. Each epidermis, stratum corneum side up, was then transferred to a 5 cm deep PYREX glass tray filled with water. Each floating epidermis was stretched essentially flat, and then removed from the water, and 2.2 cm diameter disks of each epidermis were punched out of areas having no observable surface damage. The disks were stored at 4° C. in a sealed container with water droplets to maintain their moisture.

Experimental Set-up for Electrotransport

The disks were mounted between the donor and receptor compartments, with the stratum corneum side facing the donor compartment, of a 2-compartment polycarbonate electrotransport permeation cell. The volume of each compartment was about 2 mL and the area between the two compartments, ie, the exposed area for transport, was about 1.26 cm$^2$.

An aqueous solution of the drug being transdermally delivered and the selected permeation enhancer composition, if any, was placed in the donor compartment. Dulbecco's phosphate buffered saline (approximately 0.15N NaCl, pH 7.0) was placed in the receptor compartment.

The rate of transport of drug and the electrical resistance of the skin were monitored throughout the experiments whine applying an electric current.

The cell was maintained at 32° C. by a Haake Model D1 heating block/water bath. The electrodes were connected to a galvanostat, which applied a constant current of 126 $\mu$A (current density of 100 $\mu$A/cm$^2$) and monitored the voltage drop across the skin by placing two Ag/AgCl junction reference electrodes, one each in the donor and receptor solutions, and measuring the voltage difference ($\Delta$V) between the electrodes.

The resistance of the skin (R) was obtained from Ohm's law:

$$R=\Delta V/i$$

where i equals the applied current (ie, 126 $\mu$A).

Example 1

Enhanced Effect of Composition of the Invention Over Either Component Alone on Agent Flux and Skin Resistance The following experiments were conducted to assess the effect of one composition of the invention, containing ethanol and dodecanol, on the transdermal delivery of sodium ketoprofen (ketoprofen anions) by electrotransport from a cathodic electrode. The electrotransport delivery of ketoprofen in the presence of various enhancers was assessed side-by-side for comparative purposes. The enhancers used were as follows: (i) ethanol alone; (ii) dodecanol alone; (iii) no enhancer, (iv) ethanol and dodecanol. The initial concentration of ketoprofen in the donor compartment was 100 mg/mL, and the donor solution had a pH (unbuffered) of 5.0 to 5.5. A silver chloride composite polymer electrode (cathode) was placed in the donor compartment, and a silver foil electrode (anode) was placed in the receptor compartment.

Each experiment was started by connecting the power source to the electrodes, and samples were automatically taken from the receptor compartment every one to two hour, except for ovenight experimentation, using an Isco Model 2230 autosampler and a metering pump. The concentration of ketoprofen in the samples was determined by high performance liquid chromatography (HPLC) using a Shimadzu Model SCL-6B chromatograph. Each run was conducted in triplicate, including the control, to minimize errors. All cells were set-up with tissue from the same cadaver. The selected permeation enhancer composition was placed in the donor compartment, while the control cell's donor compartment contained no enhancer.

Flux and voltage measurements generally reached steady state after about 4 hours of cell operation. The steady state flux values and calculated skin resistances are shown in Table 1 in normalized form, ie, all values are divided by their respective control value.

TABLE 1

Comparison of Effect on Agent Flux and Skin Resistance of Lower or Higher Alcohol Alone, and Composition of Invention

| Permeation Enhancer(s) | Normalized Ketoprofen Flux | Normalized Skin Resistance |
|---|---|---|
| Control (No Enhancer) | 1.00 | 1.00 |
| Ethanol (25% v/v) | 1.24 | 0.47 |
| Dodecanol (<100 mM) | 1.93 | 0.39 |
| Dodecanol (<100 mM) and Ethanol (20% v/v) | 10.15 | 0.06 |

As Table 1 above illustrates, the addition of ethanol alone produced a reduction in skin resistance to 0.47 with respect to 1 for the control (more than a 50% reduction in skin resistance), while the addition of dodecanol alone produced a reduction in skin resistance to 0.39 with respect to the value of 1 for the control (almost a 60% reduction in skin resistance).

The composition containing both dodecanol and ethanol, however, produced an unexpectedly greater redudion in skin resistance to only 0.06 with respect to the value of 1 for the control (a reduction in skin resistance of greater than 94%). In addition, ethanol alone increased the rate of delivery of ketoprofen by only 24%, and dodecanol alone increased it by 93%. The ethanol/dodecanol composition, representative of the invention, produced an unexpected enhancement of ketoprofen electrotransport flux, which was more than 10 times greater than the control.

Although ethanol is present in slightly different amounts when tested is alone (25% v/v) and with dodecanol (ethanol 20%v/v) as an enhancer, this difference in its concentration does not significantly alter its effect. This is confirmed in Example 2.

Example 2

Measurement of Metoclopramide Flux with Ethanol/Dodecanol as Enhancer in Comparison with Ethanol Alone as Enhancer (Comparison of Invention with Prior Art)

The experimental conditions were identical to those described in Example 1, except an aqueous solution of metoclopramide HCl, instead of sodium ketoprofen, was placed in the donor compartment. In addition, the silver chloride cathode was placed in the receptor compartment and the silver foil anode was placed in the donor compartment since metoclopramide ions are cationic as opposed to ketoprofen ions which are anionic. The concentration of metoclopramide in the donor solution was about 100 mg metoclopramide/mL, and saline pH 7 was placed in the receptor compartment. The system was maintained at 32° C. and a constant electric current of 100 $\mu A/cm^2$ was applied throughout the procedure.

All runs had the same concentration of agent and other conditions, except for the following shown in Table 2.

TABLE 2

Content of Enhancer (Ethanol), Metoclopramide Flux and Cell Voltage

| # | Enhancer Type | Amt (wt %) | n | Normalized Metoclopramide Mass Flux (after 5 hrs) | Normalized Skin Resistance (after 5 hrs) |
|---|---|---|---|---|---|
| 1 | None | 0 | 1 | 1.00 | 1.00 |
| 2 | Ethanol | 10 | 3 | 0.86 | 1.32 |
| 3 | Ethanol | 20 | 3 | 0.73 | 1.13 |
| 4 | Ethanol | 30 | 3 | 0.93 | 1.26 |
| 5 | Dodecanol Ethanol | 2 30 | 3 | 1.55 | 0.50 |

The mass flux and skin resistance values were normalized versus the control. The second column from the right shows the normalized values versus the electrotransport flux of metoclopramide in the absence of any permeation enhancer (first line). The skin resistance (which was calculated from the measured cell voltage $\Delta V$ using Ohm's law, $R=i/\Delta V$) was also normalized with respect to the value obtained by electrotransport of metoclopramide in the absence of any permeation enhancer (rightmost column). These values have been provided to permit a comparison with the values for the permeation enhancing compositions shown in Table 1. For example, when dodecanol was utilized in the presence of 30 wt% ethanol, the electrotransport mass flux of metoclopramide was enhanced by over 50% and the skin resistance was lowered to one-half the resistance of the control. However, the use of ethanol alone as a flux enhancer is shown in Table 2 not to enhance, but to actually decrease, the mass flux of metoclopramide and increase the resistance of the skin during electrotransport delivery of metoclopramide.

Having thus generally described the invention, and described in detail certain preferred embodiments thereof, it will be readily apparent that various modifications to the invention may be made by those skilled in the art without departing from the scope of this invention, which is limited only by the following claims.

We claim:

1. A transdermal electrotransport composition, comprising:

an agent in a form suitable for electrotransport delivery;
about 0.01 to 100 mM of at least one $C_8$–$C_{14}$ linear, branched, cyclic, or aromatic alcohol or unsaturated derivatives thereof, or mixtures thereof; and
about 0.5 to 30% (v/v) of at least one $C_2$–$C_4$ alcohol or unsaturated derivatives thereof, or mixtures thereof.

2. A transdermal electrotransport composition obtained by combining:

an agent in a form suitable for electrotransport delivery;

about 0.01 to 100 mM of at least one $C_8$–$C_{14}$ linear, branched, cyclic, or aromatic alcohol or unsaturated derivatives thereof, or mixtures thereof; and about 0.5 to 30% (v/v) of at least one $C_2$–$C_4$ alcohol or unsaturated derivatives thereof, or mixtures thereof.

3. A transdermal electrotransport composition, comprising:

an agent in a form suitable for electrotransport delivery;

about 0.01 to 100 mM of at least one $C_8$–$C_{14}$ linear, branched, cyclic, or aromatic alcohol or unsaturated derivatives thereof, or mixtures thereof; and about 0.5 to 30% (v/v) of at least one $C_2$–$C_4$ alcohol selected from the group consisting of ethanol, 1-propanol, 2-propanol, 1-butanol, 2-butanol, 1-butyl alcohol, and unsaturated derivatives thereof.

4. The composition of claim 1, 2, or 3, further comprising an aqueous solvent.

5. The composition of claim 1, 2, or 3, wherein the $C_2$–$C_4$ alcohol comprises ethanol.

6. The composition of claim 1, 2, or 3, wherein the $C_8$–$C_{14}$ alcohol comprises dodecanol.

7. The composition of claim 6, wherein the dodecanol comprises 1-dodecanol.

8. The composition of claim 1 or 2, wherein the agent suitable for electrotransport delivery is a beneficial pharmaceutically acceptable agent.

9. The composition of claim 1 or 2, wherein the agent has a molecular weight of at least 300 daltons.

10. The composition of claim 1 or 2, wherein the agent is selected from a group consisting of peptides, proteins, and polypeptides.

11. The composition of claim 1, 2, or 3, wherein the $C_8$–$C_{14}$ alcohol or unsaturated derivative thereof is present in an amount of about 1–50 mM; and the $C_2$–$C_4$ alcohol or unsaturated derivative thereof is present in an amount of about 10–25% (v/v).

12. The composition of claim 1, 2, or 3, wherein the $C_8$–$C_{14}$ alcohol comprises dodecanol, and the $C_2$–$C_4$ alcohol comprises ethanol.

* * * * *